United States Patent [19]

Young et al.

[11] 3,959,491

[45] May 25, 1976

[54] STABLE HUMAN SKIN COSMETIC COMPOSITION CONTAINING MILK

[75] Inventors: Henry Y. Young, Delmar, N.Y.; Edward Henderson, deceased, late of New York, N.Y., by Kathryn S. Henderson, executrix

[73] Assignee: Stiefel Laboratories, Inc., Oak Hill, N.Y.

[22] Filed: Oct. 29, 1974

[21] Appl. No.: 518,808

[52] U.S. Cl. .............................. 424/359; 424/249; 424/317; 424/365
[51] Int. Cl.² ........................................ A61K 7/48
[58] Field of Search ........................... 424/359, 365

[56] References Cited
UNITED STATES PATENTS

| | | | |
|---|---|---|---|
| 3,124,510 | 3/1964 | Rosenberg | 424/359 X |
| 3,340,153 | 9/1967 | Kast | 424/365 |
| 3,483,008 | 12/1969 | Herr | 424/359 X |
| 3,628,974 | 12/1971 | Battista | 424/359 X |

FOREIGN PATENTS OR APPLICATIONS

| | | | |
|---|---|---|---|
| 548,382 | 10/1942 | United Kingdom | 424/359 |

*Primary Examiner*—Sam Rosen
*Assistant Examiner*—Vera C. Clarke
*Attorney, Agent, or Firm*—Pennie & Edmonds

[57] ABSTRACT

A cosmetic composition for topical application to human skin comprises from 40 to 80 percent by weight sterilized fluid milk containing from about 7 to 18 percent fat and from about 8 to 11 percent non-fat solids, from 1 to 5 percent by weight of at least one fatty acid (for example, stearic acid), from 2.5 to 10 percent by weight of at least one triglyceride ester of a saturated fatty acid (for example, glycerol monostearate), from 5 to 15 percent by weight of at least one alkyl ester of a saturated fatty acid (for example, isopropyl palmitate), from 5 to 15 percent by weight of at least one alkane diol (for example, propylene glycol), from 0.1 to 0.5 percent by weight a salt of ethylenediamine tetraacetic acid (for example, disodium ethylenediamine tetraacetate dihydrate), from 0.1 to 0.5 percent by weight sorbic acid, from 0.3 to 0.5 percent by weight 1-(3-chloroallyl)-3,5,7-triaza-1-azoniaadomantane chloride, and the balance essentially water.

8 Claims, No Drawings

STABLE HUMAN SKIN COSMETIC COMPOSITION CONTAINING MILK

BACKGROUND OF THE INVENTION

1. Field of the Invention

This invention relates to cosmetic compositions, and in particular to a composition containing fluid milk as one of its principal constituents.

2. Prior Art

Milk, and cosmetic compositions containing milk, have long been recognized as having a beneficial effect when applied to the human skin. Moreover, whole fluid milk which still contains its natural fats (butterfat) is regarded as more beneficial to the skin than skim or non-fat milk and much more beneficial than dry milk solids or liquid milk reconstituted from dry milk solids. However, fresh fluid milk contains a variety of natural enzymes and is a rich nutrient for the growth of bacteria and other organisms which contribute to the rapid souring and short shelf life of fluid milk and products containing fluid milk. As a result, untreated fresh milk can not be employed in cosmetic compositions which are normally stored at room temperature and are required to have a useful shelf life of several years or more.

The souring and spoilage of fluid milk can be inhibited and its shelf life extended by such treatment as pasteurization or sterilization (especially, pasteurization under conditions which insure the complete destruction of all enzymes and microorganisms contained in the milk) if the pasteurized or sterilized milk is stored under refrigeration and consumed within a few days, or a few weeks, of the treatment. However, it has not heretofore been possible to employ fluid milk in ordinary cosmetic compositions, even if the milk is pasteurized or sterilized, because of the necessity for storing such compositions at room temperature for long periods of time.

The spoilage of fluid milk can also be inhibited by the inclusion of large dosages of anti-enzyme (anti-oxidants), bactericidal and fungicidal agents in the milk. However, the anti-enzyme, bactericidal and fungicidal agents heretofore employed (for example, formaldehyde and sodium disulfite) are either powerful skin irritants or allergens or must be used in such large amounts that the resulting milk product is unsuitable for use in or as a cosmetic. At best, only a very small amount of fluid milk (less than 10%) treated with conventional preservatives can be incorporated in cosmetic compositions before the quantity of preservative agent required to be present reaches unacceptable levels.

As an alternative to the use of fluid milk, it has heretofore been proposed that dry milk solids, and usually non-fat dry milk solids, be employed as an ingredient in cosmetic compositions. However, as previously noted, cosmetic compositions prepared from dry milk solids are not nearly as beneficial to the skin as are cosmetic compositions prepared from whole fluid milk. Moreover, in order to prevent spoilage and to extend the shelf life of these compositions it is necessary to include preservative agents that are irritating or allergenic to the skin in these compositions. As a result, cosmetic compositions containing dry milk solids have not met with success.

In view of the recognized superiority for cosmetic purposes of whole fluid milk containing a high proportion of natural milk fats, as compared to skim milk and dry milk solids, we have carried out an intensive investigation of the problems encountered in preparing cosmetic compositions containing whole fluid milk. As a result of our investigation we have discovered that cosmetic compositions can be prepared which contain a much higher proportion of whole fluid milk and which have a shelf life under ordinary conditions of storage far in excess of comparable milk-containing cosmetics heretofore known, provided certain novel formulation criteria are observed. Specifically, we have discovered that the high milk content and the long shelf life of the cosmetic composition of the invention are attributable in large measure to the use of sterilized fluid milk containing added milk fats and to the synergistic effect of two specific preservative agents neither one of which, by itself, is capable of achieving the results obtained when the two are employed together.

SUMMARY OF THE INVENTION

The cosmetic composition of the invention is advantageously prepared from sterilized fluid milk the butterfat content of which has been augmented by the addition thereto of an approximately equal amount of cream. The composition comprises from about 40 to 80 percent by weight of sterilized fluid milk containing from about 7 to 18 percent fat, from about 8 to 11 percent non-fat solids and the balance essentially water. In addition, the composition contains from 1 to 5 percent by weight of at least one acidifier and buffer selected from the group consisting of saturated fatty acids having from 12 to 20 carbon atoms, from 2.5 to 10 percent by weight of at least one emulsifier and stabilizer selected from the group consisting of triglyceride esters of saturated fatty acids having from 16 to 18 carbon atoms, from 5 to 15 percent by weight of at least one alkyl ester of a saturated fatty acid in which the alkyl radical has from 2 to 18 carbon atoms and the fatty acid has from 12 to 20 carbon atoms, from 5 to 15 percent by weight of at least one stabilizer selected from the group consisting of alkane diols having from 2 to 6 carbon atoms, and from 0.1 to 0.5 percent by weight of a sequestering agent selected from the group consisting of ethylenediamine tetraacetic acid salts. The composition also must contain from 0.1 to 0.5 percent by weight sorbic acid and from 0.3 to 0.5 percent by weight 1-(3-chloroallyl)-3,5,7-triaza-1-azoniaadamantane chloride, the latter two constituents acting as enzyme denaturants and antibacterial preservatives in the composition. The composition may also contain minor amounts of an opacifier and a fragrance, and it may contain additional water (apart from that present in the fluid milk).

DETAILED DESCRIPTION

Cosmetic compositions, and in particular cosmetic creams and lotions, are applied to the skin for a number of purposes — for example, to lubricate or moisturize the skin, to alleviate or compensate for excessively dry or oily skin, to provide a foundation for other cosmetic preparations and the like. Depending upon its intended purpose, such compositions are required to meet certain criteria established by the formulator with respect to stability, shelf life and emollient properties (for example, lubricity, smoothness, body, lipids to water ratio and the like), and this determines the kinds and quantities of the ingredients that go into the composition. Whole fluid milk has long been recognized as having a beneficial effect when applied to human skin, and many attempts have heretofore been made to incorporate appreciable quantities of milk in cosmetics that are applied to the skin. However, these earlier attempts to prepare stable and long-lived cosmetic compositions containing a cosmetically effective amount of milk have not met with success for the reasons hereinbefore discussed. The cosmetic composition of the present invention contains a high proportion of whole fluid milk and milk fats, it is stable and possesses a long shelf life, and it has highly desirable emollient and skin conditioning properties, as herein described.

The principal ingredient of our new cosmetic composition is whole fluid milk containing a high proportion of natural milk fats, and advantageously the composition is prepared from sterilized fluid milk the milk fat content of which has been augmented by the addition thereto of an approximately equal amount of cream. Specifically, we have found that unless the fluid milk contains at least about 7 percent by weight milk fats and unless the cosmetic composition contains at least about 40 percent by weight of such milk, the composition will not meet the emollient and lipid criteria established for our cosmetic. Moreover, we have found that if the fluid milk contains more than about 18 percent by weight milk fats or if the composition contains more than about 80 percent by weight milk, the composition is of uncertain stability and shelf life. Accordingly, the fluid milk constituent of the composition contains from about 7 to 18 percent by weight milk fats and from about 8 to 11 percent by weight non-fat milk solids (the balance of the fluid milk being essentially water), and the amount of fluid milk present in the composition may range from about 40 to 80 percent by weight of the composition. The term "fluid milk" as employed herein refers to natural cows milk that contains its normal complement of milk fats (about 3.5 to 4.5 percent) augmented by the addition thereto of up to an approximately equal amount of cream. The term "sterilized" as employed herein refers to such fluid milk that has been treated to destroy or render inactive all of the enzymes and microorganisms normally present in the milk, and it includes such treatments as pasteurization and irradiation.

In addition to its whole milk content, the composition of the invention contains a variety of other ingredients for adjusting and buffering the acidity of the composition, for emulsifying and stabilizing the composition, for modifying or enhancing the smoothness and spreadability of the composition, for sequestering undesirable cations that may be present in the composition, and most importantly for prolonging the shelf life of the composition by preventing enzyme and bacterial activity therein.

The composition advantageously should have the same approximate acidity as the skin mantle, and to this end from about 1 to 5 percent by weight of at least one saturated fatty acid having from 12 to 20 carbon atoms is incorporated in the composition to adjust the pH of the composition to between about 5 to 5.5, the saturated fatty acid also serving as a buffer to maintain the pH of the composition within this range. We presently prefer to use stearic acid (triple pressed grade) as the acidifier and buffer for the composition. However, we have found that lauric acid, myristric acid, palmitic acid and arachidic acid may also be used for this purpose.

The composition inherently contains a substantial amount of water as well as milk fats and other lipids, and these aqueous and lipid constituents must be present in the form of an emulsion that is stable for the useful life of the composition. In order to insure the maintenance of a stable emulsion for the life time of the composition, we have found that the composition should advantageously contain from about 2.5 to 10 percent by weight of at least one triglyceride ester of a saturated fatty acid having from 16 to 18 carbon atoms. We presently prefer to use glycerol monostearate as the emulsifier and stabilizer although glycerol distearate, glycerol tristearate, glycerol monopalmitate, glycerol dipalmitate and glycerol tripalmitate may also be used for this purpose. In addition, we have found it advantageous to incorporate from about 5 to 15 percent by weight of one or more alkane diols having from 2 to 6 carbon atoms in the composition as a stabilizer therefor. We presently prefer to use propylene glycol as the alkane diol stabilizer although ethylene glycol, butylene glycol, pentylene glycol and hexylene glycol may also be used for this purpose.

In order to enhance the spreadability and smoothness of the composition advantageously contains from about 5 to 15 percent by weight of at least one alkyl ester of a saturated fatty acid in which the alkyl radical has from 2 to 18 carbon atoms and the saturated fatty acid has from 12 to 20 carbon atoms. We presently prefer to use isopropyl palmitate either by itself or in admixture with other alkyl esters of saturated fatty acids. However, depending on the tactile properties desired of the finished product, such diverse fatty acid esters as ethyl laurate, ethyl palmitate, ethyl stearate, isopropyl mysristate, isopropyl stearate butyl palmitate, butyl stearate, pentyl laurate, hexyl palmitate, octyl palmitate, dodecyl stearate, hexadecyl stearate, octadecyl myristate and others may be used for this purpose.

The presence of trace amounts of certain heavy metal ions in the composition may adversely affect the color of the composition or serve as catalysts for unwanted reactions in the composition. Accordingly we have found it to be advantageous to include from 0.1 to 0.5 percent by weight of ethylene diamine tetraacetic acid and salts of this acid in the composition to sequester and render harmless such heavy metal cations such as copper and iron ions. We presently prefer to use for this purpose disodium ethylene diaminetetraacetate dihydrate.

In order to prevent souring and spoilage of the milk-containing composition, the milk employed should not only be sterilized but the composition itself must contain antibacterial and antifungal preservatives and enzyme denaturants. Many substances that would serve this purpose in non-cosmetic compositions cannot be used in cosmetic compositions because of their irritating and possibly allergic effect on the skin. We have found that sorbic acid (2,4-hexadienoic acid) is an effective enzyme denaturant, yeast inhibiter, bactericide and fungicide when used in our composition. However, the amount of sorbic acid required to be present to provide a useful shelf life for the composition is in excess of the amount considered by us to be acceptable (more than about 0.5 percent by weight). On the other hand, we have found that an amount of less than about 0.15 percent by weight of sorbic acid is wholly ineffective. Similarly, we have found that 1-(3-chloroallyl)-3,5,7-triaza-1-azoniaadamantane chloride (hereinafter referred to as Dowicil 200, a product of the Dow Chemical Co.) is also an effective enzyme denaturant, bactericide and fungicide when used in the present composition. However, when used by itself it is necessary to employ an amount of Dowicil 200 in excess of that which we consider acceptable (more than about 0.5 percent by weight) in order to obtain a product having a useful shelf life of two or more years.

As a result of our investigations, we have discovered that if sorbic acid and Dowicil 200 are employed jointly in the composition, the amount of either of these substances required to obtain a product having a useful shelf life may be sufficiently small so that neither exceeds the amount we consider to be acceptable in our composition, provided the composition contains at least about 0.15 percent sorbic acid and at least about 0.3 percent by weight Dowicil 200. Moreover, we have made the surprising and completely unexpected discovery that the combination of sorbic acid and Dowicil 200 have a marked synergistic effect on their preservative activity in that the shelf life of the composition containing both preservative substances is substantially greater than the shelf life of the same composition containing only one or the other of these substances, albeit in substantially larger quantities. Accordingly, the composition of the invention contains from 0.15 to 0.5 percent by weight sorbic acid and from 0.3 to 0.5 percent by weight Dowicil 200.

The following examples are illustrative but not limitative of milk-containing cosmetic compositions prepared in accordance with the invention.

The composition may advantageously be prepared by first mixing 1.5 parts by weight stearic acid (triple pressed grade), 3.8 parts by weight glycerol monostearate, 0.25 parts by weight polyethylene glycol 6000 distearate, and 11.25 parts by weight isopropyl palmitate in a first vessel, the mixture then being heated to 70°C and thoroughly blended together. In a second vessel 0.2 parts by weight of disodium ethylenediamine tetraacetate dihydrate are dissolved in 72 parts by weight of a sterilized homogenous mixture of milk and cream containing 15% by weight milk fats and 8 percent by weight non-fat solids. The temperature of the milk solution is raised to 70°C. and then added to the mixture in the first vessel with continued stirring to obtain a smooth emulsion. The emulsion is then cooled to about 45°C., and 0.35 parts by weight of a fragrance is added to the emulsion with stirring. In a third vessel 0.15 parts by weight of hexadienoic acid (sorbic acid) and 0.5 parts by weight of 1-(3-chloroallyl)-3,5,7-triaza-1-azoniaadamantane E chloride (hereinafter referred to as Dowicil 200) are dissolved in 10 parts by weight of propylene glycol, and this solution is added to the emulsion in the first vessel. The emulsion is stirred until the product reaches a temperature of 30°C. at which point it is ready for use. This milk-containing cosmetic product had the following composition:

EXAMPLE I

| | |
|---|---|
| Fluid milk, sterilized | 72.00 |
| 15% milk fat | |
| 8% non-fat solids | |
| Balance water | |
| Stearic acid, triple pressed | 1.50 |
| Glycerol monostearate | 3.80 |
| Polyethylene glycol 6000 distearate | 0.25 |
| Isopropyl palmitate | 11.25 |
| Propylene glycol | 10.00 |
| Disodium ethylenediamine tetraacetate dihydrate | 0.20 |
| Sorbic acid | 0.15 |
| Dowicil 200 | 0.50 |

EXAMPLE I-continued

| | |
|---|---|
| Fragrance | 0.35 |

Other compositions of the invention prepared in accordance with the foregoing procedure have the following compositions:

EXAMPLE II

| | |
|---|---|
| Fluid milk, sterilized | 78.0 |
| 16% milk fat | |
| 9% non-fat solids | |
| Balance water | |
| Myristic acid | 0.5 |
| Stearic Acid | 2.0 |
| Glycerol tripalmitate | 2.5 |
| Butyl stearate | 6.0 |
| Hexadecyl stearate | 2.5 |
| Propylene glycol | 7.6 |
| Disodium ethylenediamine tetraacetate dihydrate | 0.2 |
| Sorbic acid | 0.3 |
| Dowicil 200 | 0.4 |

EXAMPLE III

| | |
|---|---|
| Fluid milk, sterilized | 46.0 |
| 18% milk fat | |
| 10% non-fat solids | |
| Balance water | |
| Palmitic acid | 3.5 |
| Glycerol distearate | 7.5 |
| Polyethylene glycol 6000 distearate | 1.25 |
| Ethyl palmitate | 12.5 |
| Hexadecyl stearate | 2.5 |
| Hexylene glycol | 12.00 |
| Disodium ethylenediamine tetraacetate dihydrate | 0.20 |
| Sorbic acid | 0.25 |
| Dowicil 200 | 0.50 |
| Fragrance | 0.35 |
| Water | 13.45 |

EXAMPLE IV

| | |
|---|---|
| Fluid milk, sterilized | 63.0 |
| 12% milk fat | |
| 8% non-fat solids | |
| Balance water | |
| Lauric acid | 1.0 |
| Stearic acid | 1.0 |
| Glycerol monopalmitate | 8.0 |
| Polyethylene glycol 6000 distearate | 0.5 |
| Isopropyl myristate | 8.5 |
| Dodecyl stearate | 6.7 |
| Butylene glycol | 10.0 |
| Disodium ethylenediamine tetraacetate dihydrate | 0.2 |
| Sorbic acid | 0.4 |
| Dowicil 200 | 0.4 |
| Fragrance | 0.3 |

EXAMPLE V

| | |
|---|---|
| Fluid milk, sterilized | 58.0 |
| 10% milk fat | |
| 9% non-fat solids | |
| Balance water | |
| Myristic acid | 0.5 |
| Palmitic acid | 1.5 |
| Stearic Acid | 2.0 |
| Glycerol tripalmitate | 8.0 |
| Octyl palmitate | 9.0 |
| Hexadecyl stearate | 5.4 |
| Propylene glycol | 15.0 |
| Disodium ethylenediamine tetraacetate dihydrate | 0.1 |
| Sorbic acid | 0.2 |
| Dowicil 200 | 0.3 |

EXAMPLE VI

| | |
|---|---|
| Fluid milk, sterilized | 68.0 |
| 18% milk fat | |
| 11% non-fat solids | |
| Balance water | |
| Stearic acid | 2.0 |
| Glycerol dipalmitate | 6.5 |
| Hexyl palmitate | 10.0 |
| Hexadecyl stearate | 3.5 |
| Butylene glycol | 9.0 |

| -continued | |
|---|---|
| Sorbic acid | 0.3 |
| Dowicil 200 | 0.5 |
| Fragrance | 0.2 |

The cosmetic compositions of the invention contain from 40 to 80 percent by weight, and preferably from 70 to 75 percent by weight, of sterilized fluid milk enriched with cream. We know of no other cosmetic preparation which contains such a high proportion of fluid milk and cream. Despite the unusually high fluid milk content of the composition, it can be stored without refrigeration for the lengthy periods of time normally required of ordinary commercial cosmetic preparations. Neither off-odor nor bacterial spoilage occurs. This remarkable performance is the result of the synergistic preservative activity of sorbic acid and Dowicil 200 when incorporated in the composition in the proportions specified. The composition passes the USP Microbial challenge Test against high inocula of *Staplylococcus Aureus*, *Pseudomonas Aeruginosia*, *Salmonella Choleraesuis* and *Aspergillus Niger*. The combination of sorbic acid and Dowicil 200 effectively prevents malodor formation during storage by denaturing the milk enzymes. When either sorbic acid or Dowicil 200 are absent from the composition, the preservative action against microbial contamination and the prevention of the development of off-odors during storage at room temperature and at elevated temperatures is greatly diminished. It requires the dual synergistic action of both of these preservative ingredients to obtain the highly unexpected results. The high milk and cream content of our composition confers superior emolliency performance. In controlled clinical tests all persons who have used the composition have been highly enthusiastic and report that it is particularly useful for the relief of dry skin.

We claim:

1. A cosmetic composition for topical application to human skin comprising
   from 40 to 80 percent by weight sterilized fluid milk containing from about 7 to 18 percent milk fats, from about 8 to 11 percent non-fat solids and the balance essentially water,
   from 1 to 5 percent by weight of at least one acidifier and buffer which is a fatty acid having from 12 to 20 carbon atoms,
   from 2.5 to 10.0 percent by weight of at least one emulsifier and stabilizer which is a triglyceride ester of a saturated fatty acid having from 16 to 18 carbon atoms,
   from 5 to 15 percent by weight of at least one alkyl ester of a saturated fatty acid in which the alkyl radical has from 2 to 18 carbon atoms and the fatty acid has from 12 to 20 carbon atoms,
   from 5 to 15 percent by weight of at least one stabilizer which is a alkane diol having from 2 to 6 carbon atoms,
   from 0.1 to 0.5 percent by weight of a sequestering agent selected from the group consisting of ethylenediamine tetraacetic acid and salts thereof,
   from 0.1 to 0.5 percent by weight sorbic acid, and
   from 0.3 to 0.5 percent by weight 1-(3-chloroallyl)-3,5,7-triaza-1-azoniaadamantane chloride.

2. The cosmetic composition according to claim 1 in which the composition contains from 70 to 75 percent by weight sterilized fluid milk.

3. The cosmetic composition according to claim 1 in which the composition comprises:

| | | |
|---|---|---|
| Fluid milk, sterilized | 72.00 | % by weight |
|   15% milk fat | | |
|   8% non-fat solids | | |
|   Balance water | | |
| Stearic acid, triple pressed | 1.50 | " |
| Glycerol monostearate | 3.80 | " |
| Polyethylene glycol 6000 distearate | 0.25 | " |
| Isopropyl palmitate | 11.25 | " |
| Propylene glycol | 10.00 | " |
| Disodium ethylenediamine tetraacetate dihydrate | 0.20 | " |
| Sorbic acid | 0.15 | " |
| 1-(3-chloroallyl)-3,5,7-triaza-1-azoniaadamantane chloride | 0.50 | " |
| Fragrance | 0.35 | ". |

4. The cosmetic composition according to claim 1 in which the composition comprises:

| | | |
|---|---|---|
| Fluid milk, sterilized | 78.0 | % by weight |
|   16% milk fat | | |
|   9% non-fat solids | | |
|   Balance water | | |
| Myristic acid | 0.5 | " |
| Stearic Acid | 2.0 | " |
| Glycerol tripalmitate | 2.5 | " |
| Butyl stearate | 6.0 | " |
| Hexadecyl stearate | 2.5 | " |
| Propylene glycol | 7.6 | " |
| Disodium ethylenediamine tetraacetate dihydrate | 0.2 | " |
| Sorbic acid | 0.3 | " |
| 1-(3-chloroallyl)-3,5,7-triaza-1-azoniaadamantane chloride | 0.4 | ". |

5. The cosmetic composition according to claim 1 in which the composition comprises:

| | | |
|---|---|---|
| Fluid milk, sterilized | 46.0 | % by weight |
|   18% milk fat | | |
|   10% non-fat solids | | |
|   Balance water | | |
| Palmitic acid | 3.5 | " |
| Glycerol distearate | 7.5 | " |
| Polyethylene glycol 6000 distearate | 1.25 | " |
| Ethyl palmitate | 12.5 | " |
| Henadecyl stearate | 2.5 | " |
| Hexylene glycol | 12.00 | " |
| Disodium ethylenediamine tetraacetate dihydrate | 0.20 | " |
| Sorbic acid | 0.25 | " |
| 1-(3-chloroallyl)-3,5,7-triaza-1-azoniaadamantane chloride | 0.50 | " |
| Fragrance | 0.35 | " |
| Water | 13.45 | ". |

6. The cosmetic composition according to claim 1 in which the composition comprises:

| | | |
|---|---|---|
| Fluid milk, sterilized | 63.0 | % by weight |
|   12% milk fat | | |
|   8% non-fat solids | | |
|   Balance water | | |
| Lauric acid | 1.0 | " |
| Stearic acid | 1.0 | " |
| Glycerol monopalmitate | 8.0 | " |
| Polyethylene glycol 6000 distearate | 0.5 | " |
| Isopropyl myristate | 8.5 | " |
| Dodecyl stearate | 6.7 | " |
| Butylene glycol | 10.0 | " |
| Disodium ethylenediamine tetraacetate dihydrate | 0.2 | " |
| Sorbic acid | 0.4 | " |
| 1-(3-chloroallyl)-3,5,7-triaza-1-azoniaadamantane chloride | 0.4 | " |

-continued

| | | |
|---|---|---|
| Fragrance | 0.3 | ". |

7. The cosmetic composition according to claim 1 in which the composition comprises:

| | | |
|---|---|---|
| Fluid milk, sterilized | 58.0 | % by weight |
| 10% milk fat | | |
| 9% non-fat solids | | |
| Balance water | | |
| Myristic acid | 0.5 | " |
| Palmitic acid | 1.5 | " |
| Stearic acid | 2.0 | " |
| Glycerol tripalmitate | 8.0 | " |
| Octyl palmitate | 9.0 | " |
| Hexadecyl stearate | 5.4 | " |
| Propylene glycol | 15.0 | " |
| Disodium ethylenediamine tetraacetate dihydrate | 0.1 | " |
| Sorbic acid | 0.2 | " |
| 1-(3-chloroallyl)-3,5,7-triaza-1-azoniaadamantane | | |

-continued

| | | |
|---|---|---|
| chloride | 0.3 | ". |

8. The cosmetic composition according to claim 1 in which the composition comprises:

| | | |
|---|---|---|
| Fluid milk, sterilized | 68.0 | % by weight |
| 18% milk fat | | |
| 11% non-fat solids | | |
| Balance water | | |
| Stearic acid | 2.0 | " |
| Glycerol dipalmitate | 6.5 | " |
| Hexyl palmitate | 10.0 | " |
| Hexadecyl stearate | 3.5 | " |
| Butylene glycol | 9.0 | " |
| Sorbic acid | 0.3 | " |
| 1-(3-chloroally)-3,5,7-triaza-1-azoniaadamantane chloride | 0.5 | " |
| Fragrance | 0.2 | ". |

* * * * *